United States Patent
Rivard et al.

(10) Patent No.: US 6,554,831 B1
(45) Date of Patent: Apr. 29, 2003

(54) MOBILE DYNAMIC SYSTEM FOR TREATING SPINAL DISORDER

(75) Inventors: Charles-Hilaire Rivard, St. Lambert (CA); Ariel Dujovne, Cote St. Luc (CA)

(73) Assignee: Hopital Sainte-Justine, Montréal (CA)

( * ) Notice: Subject to any disclaimer, the term of this patent is extended or adjusted under 35 U.S.C. 154(b) by 250 days.

(21) Appl. No.: 09/653,328

(22) Filed: Sep. 1, 2000

(51) Int. Cl.$^7$ ............................................. A61B 17/56
(52) U.S. Cl. ........................................ 606/61; 606/72
(58) Field of Search ......................... 606/61, 59, 60, 606/72, 74, 103; 623/17.11, 17.15, 17.16; 403/59, 61, 13, 92

(56) References Cited

U.S. PATENT DOCUMENTS

| | | |
|---|---|---|
| 4,269,178 A | 5/1981 | Keene |
| 5,084,048 A | 1/1992 | Jacob et al. |
| 5,096,327 A | 3/1992 | Ruland |
| 5,112,332 A | 5/1992 | Cozad et al. |
| 5,246,458 A | 9/1993 | Graham |
| 5,413,576 A | 5/1995 | Rivard |
| 5,480,442 A | 1/1996 | Bertagnoli |
| 5,498,262 A * | 3/1996 | Bryan .......................... 606/53 |
| 5,591,166 A * | 1/1997 | Bernhardt et al. ............ 606/60 |
| 5,628,740 A * | 5/1997 | Mullane ........................ 606/61 |
| 5,649,926 A * | 7/1997 | Howland ....................... 606/61 |
| 5,672,175 A | 9/1997 | Martin |
| 5,704,936 A | 1/1998 | Mazel |
| 5,776,135 A | 7/1998 | Errico et al. |
| 5,810,817 A * | 9/1998 | Roussouly et al. ........... 606/61 |
| 5,910,142 A | 6/1999 | Tatar |
| 6,267,765 B1 * | 7/2001 | Taylor et al. ................. 606/61 |
| 6,283,967 B1 * | 9/2001 | Troxell et al. ................ 606/61 |
| 6,306,137 B2 * | 10/2001 | Troxell ......................... 403/13 |

FOREIGN PATENT DOCUMENTS

WO    WO 99/09902    3/1999

* cited by examiner

*Primary Examiner*—Pedro Philogene
(74) *Attorney, Agent, or Firm*—Swabey Ogilvy Renault; Robert Mitchell; Kevin P. Murphy

(57) ABSTRACT

A mobile dynamic implantable spinal apparatus comprising at least one fixed bracket secured on a correcting rod and at least one mobile carrier slidably mounted on the correcting rod. The fixed bracket and the mobile carrier each include a body and a pedicle screw or a transverse process hook articulated to the body. The distribution of the degrees of freedom between the carrier and the rod, and the pedicle screws or hooks and the carrier and the fixed bracket provide a non-rigid assembly which preserves some of the natural mobility of the vertebrae and disk, and the potential growth of the spinal column.

28 Claims, 5 Drawing Sheets

MOBILE DYNAMIC SYSTEM FOR TREATING SPINAL DISORDER

BACKGROUND OF THE INVENTION

1. Field of the Invention

The present invention relates to spinal disorders and, more particularly, to a mobile dynamic system for treating spinal disorders.

2. Description of the Prior Art

Conventional implantable apparatuses for treating spinal disorders, such as scoliosis, typically include a pair of implantable rods for mounting on either side of the spinal column. Rigid transverse bars typically connect the rods together in spaced-apart parallel arrangement. Anchors in the form of hooks or screws are provided along each rod for anchoring same to the selected vertebrae. Once installed, the anchors are rigidly locked to the associated rod to prevent relative motion therebetween. Such an arrangement must be supplemented with bone grafts and the fusion of several vertebrae in order to prevent the apparatus from breaking due to the loads induced thereon. However, bone grafts and vertebrae fusion often cause serious complications throughout the patient's adult life.

Accordingly, efforts have been made to develop implantable spinal instrumentation which could sustain greater loads and, thus, eliminate the need of resorting to bone grafts and vertebrae fusion. For instance, U.S. Pat. No. 5,672,175 issued on September 30, 1997 to Martin discloses a fusionless implantable spinal instrumentation wherein the implanted rods are anchored to the spinal column with fixed central anchors and terminal dynamic anchors. Each terminal anchor is rigidly connected to a coupling member which is in turn slidably mounted to a corresponding one of the implanted rods. The coupling members can have a selected number of degree of freedom relative to the corresponding rod.

Although the implantable spinal instrumentation disclosed in the above mentioned patent constitutes a technological advancement, it has been found that there is a need for a new dynamic implantable instrumentation which could be used for treating spinal disorders.

SUMMARY OF THE INVENTION

It is therefore an aim of the present invention to provide a dynamic mobile implantable apparatus for treating spinal column disorders.

It is also an aim of the present invention to provide such a dynamic mobile implantable apparatus which allows growth of the spinal column of the patient.

It is a further aim of the present invention to provide a new dynamic spinal instrumentation system.

It is a still further aim of the present invention to provide a dynamic spinal instrumentation system which is adapted to preserve at least in part the physiological mobility of the vertebrae and the disc.

It is still a further aim of the present invention to provide a new dynamic anchoring assembly for connecting a spinal implantable rod with a bone.

It is still a further aim of the present invention to provide a dynamic cross-link for structurally connecting a pair of spinal implantable rods together.

Therefore, in accordance with the present invention, there is provided a mobile dynamic internal system for treating a disorder of a spinal column having a sagittal plane, comprising at least one implantable correcting rod for mounting on one side of a patient's spinal column, at least one fixed bracket rigidly mounted to said correcting rod, and at least one mobile carrier slidably mounted to said correcting rod, and first and second anchors respectively mounted to said mobile carrier and said fixed bracket for anchoring said correcting rod to the spinal column, wherein, once said dynamic internal system has been implanted, said first and second anchors still respectively have limited freedom of movement relative to said mobile carrier and said fixed bracket, thereby allowing said mobile carrier to slide along said correcting rod in response of movements of the spinal column.

In accordance with a further general aspect of the present invention, there is provided a mobile dynamic anchoring assembly for connecting an implantable rod with a bone, comprising a carrier adapted to be mounted to an implantable rod for sliding movement thereon and limited pivotal movement with respect thereto about an axis perpendicular to the rod, and a bone anchor articulately connected to said carrier for allowing the mobility of said carrier to be preserved once said anchor has been engaged with a bone.

In accordance with a further general aspect of the present invention, there is provided a mobile dynamic cross-link for structurally connecting a pair of implantable spinal rods together, comprising opposed first and second ends adapted to be connected to corresponding ones of a pair of implantable spinal rods, and a point of articulation between said first and second ends to prevent the implantable spinal rods from pivoting apart while allowing any other limited relative movements therebetween.

BRIEF DESCRIPTION OF THE DRAWINGS

Having thus generally described the nature of the invention, reference will now be made to the accompanying drawings, showing by way of illustration a preferred embodiment thereof, and in which.

DESCRIPTION OF THE PREFERRED EMBODIMENTS

Throughout the text, the term "sagittal plane" is used to designate the median longitudinal plane of the spinal column dividing the same into right and left halves in a frontal plane or a back plane of the patient's body.

Figure 1:
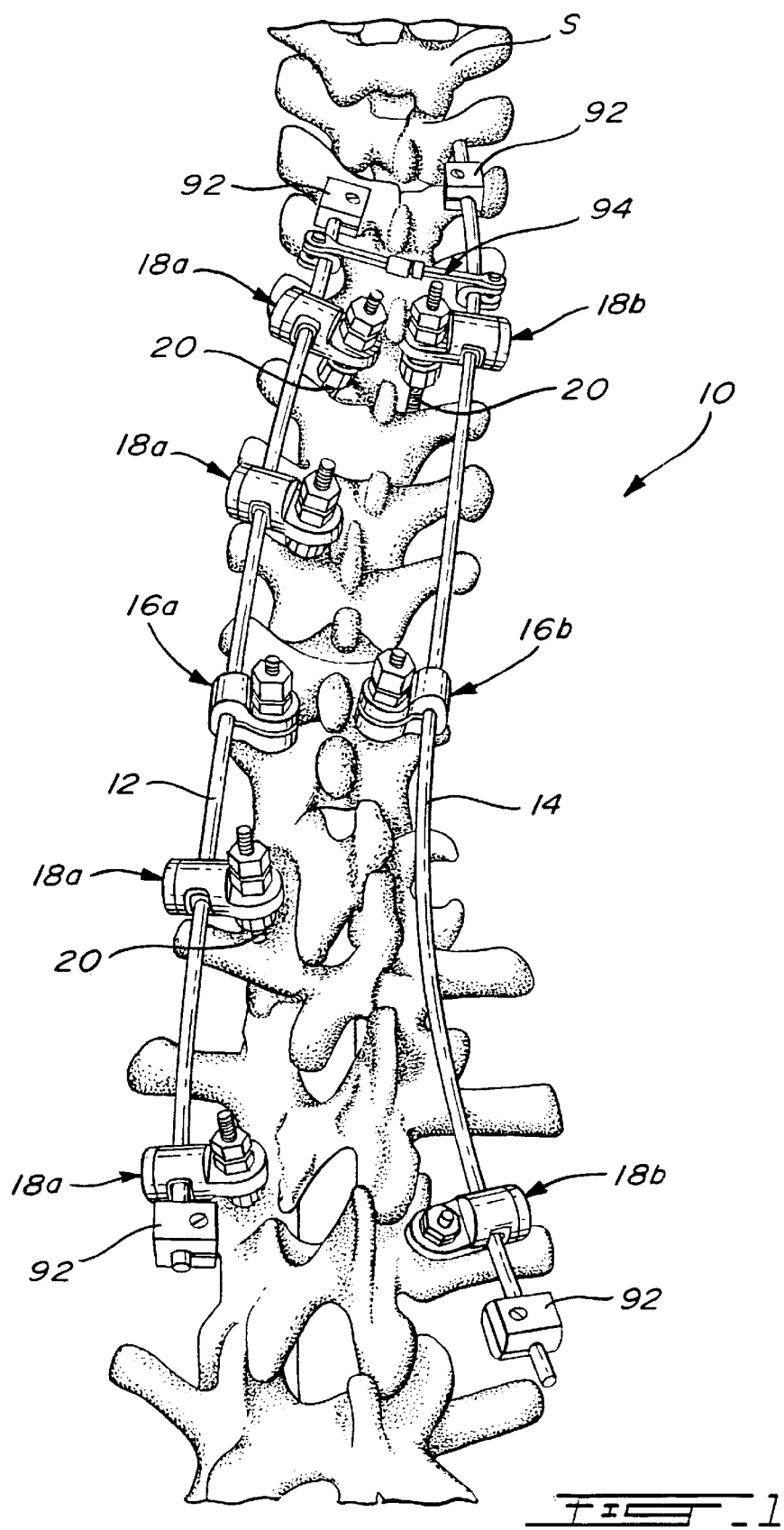
FIG. 1 is a rear elevational view of a mobile dynamic spinal instrumentation system installed on a laterally deviated portion of a patient's spinal column in accordance with a first embodiment of the present invention.

FIG. 1 illustrates a mobile dynamic implantable instrumentation system 10 for correcting various disorders of a patient's spinal column S. For instance, the mobile dynamic implantable instrumentation system 10 can be used for treating a lateral deviation of the spinal column S, such as a scoliosis. It has been found that in patients suffering from scoliosis, that the vertebrae in the curved portion of the spinal column S may be rotated horizontally due to torsional forces acting thereon. The implantable instrumentation system 10 would, as will be seen, retain the individual vertebrae in a generally realigned position approximating their position in a normal spinal column, while advantageously preserving some of the natural mobility of the vertebrae and growth potential of the bones of the spinal column S.

The dynamic implantable instrumentation system 10 illustrated in FIG. 1 generally comprises a pair of spinal implantable rods 12 and 14. Each of the rods 12 and 14 may be curved to approximate a desirable 3-dimensional curve of the portion of the spinal column in which the system 10 is to be implanted. The rods 12 and 14 are preferably made of a metal alloy, such as titanium or stainless steel. One of the rods 12 and 14 is used as a correcting rod to translate and maintain the vertebrae in a correct alignment, while the other rod acts as a stabilizer for the correcting rod. It is noted that for certain disorders, for instance, where the loads exerted on the correcting rod are less important, it might be possible to use a single rod instead of a pair of rods.

In the illustrated example, the rod 12 extends through a central fixed bracket 16a and a selected number of mobile carriers 18a disposed on either side of the central fixed bracket 16a. Similarly, according to the illustrated embodiment, the rod 14 extends through a central fixed bracket 16b and a pair of mobile carriers 18b disposed on opposed sides of the central fixed bracket 16b. It is noted that depending on the spinal disorder to be treated, the mobile carriers 18a and 18b could be placed on a same side of the fixed brackets 16a and 16b rather than on opposed sides thereof, as illustrated in FIG. 1. Anchors, such as pedicle screws 20, are articulated to the central fixed brackets 16a, 16b and mobile carriers 18a, 18b so as to maintain the rods 12 and 14 in a corrected position in opposition to the deformation forces of the spinal column S, while allowing some of the natural physiological movements of the vertebrae and disc. The disposition of the fixed brackets 16a and 16b relative to the mobile carriers 18a and 18b on both rods 12 and 14, advantageously allows the patient's spinal column to grow, while the system 10 is still implanted in the patient's body.

Figure 2:
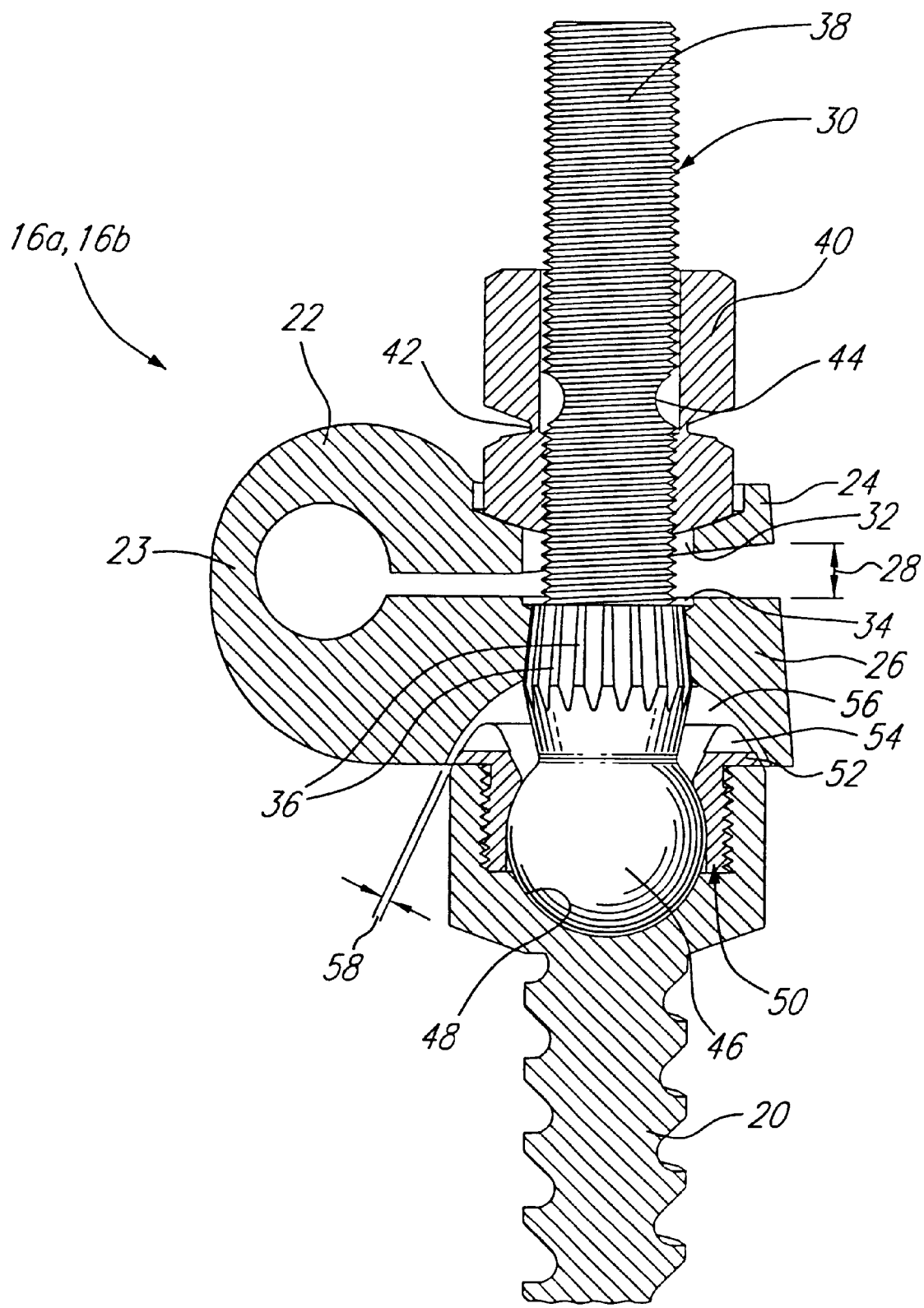
FIG. 2 is a cross-sectional view of a fixed pedicle screw bracket forming part of the mobile dynamic spinal instrumentation system of FIG. 1.

As seen in FIG. 2, each fixed bracket 16a, 16b is provided in the form of a C-shaped clamp collar 22 having an intermediate curved rod engaging portion 23 and opposed first and second ends 24 and 26 extending in parallel and defining a circumferential gap 28 therebetween. A pin 30 extends through a pair of registered through bores 32 and 34 respectively defined in the first and second ends 24 and 26 of the clamp collar 22. A plurality of axially extending splines 36 are circumferentially distributed on a tapering enlarged bottom portion of the pin 30 to mate with corresponding splines (not shown) formed in the side wall of the through bore 34. This prevents the pin 30 from rotating about a longitudinal axis thereof relative to the clamp collar 22. The pin 30 has a threaded portion 38 upon which a self-breaking and self-aligning nut 40 can be threadably engaged to press the first and second ends 24 and 26 together and, thus, fixedly secure the clamp collar 22 to one of the rods 12 and 14 with the pin 30 extending generally perpendicularly to a longitudinal axis of the associated rod 12, 14 and being spaced laterally therefrom. The self-breaking and self aligning nut 40 is provided with an annular weak region 42 which is adapted to break at a predetermined tightening torque. A weak region 44 is also defined in the threaded portion of the pin 30 to facilitate removal of the extra-length thereof once the self-breaking and self-aligning nut 40 has been broken while being tightened to transmit the desired clamping force to the clamp collar 22. The extra-length of the pin 30, i.e. the portion of the pin 30 between the weak region 44 and the free distal end of the threaded portion 38, is used to facilitate the engagement of the pin 30 within the through bores 32 and 34.

The pin 30 is provided at one end thereof opposite the threaded portion 38 with a ball formation 46 adapted to be received in a socket 48 defined in the head of each pedicle screw 20 to permanently permit limited relative movements between the collar clamp 22 and the associated pedicle screw 20 in three degrees of freedom. Axial removal of the ball formation 46 from the socket 48 is prevented by a hollow retaining cap 50 threadably engaged in the socket 48 and through the central portion of which the pin 30 extends outwardly.

The retaining cap 50 has a top annular flange 52 which is adapted to bear against the underlying top surface of the head of the associated pedicle screw 20 and from which a segment of a sphere 54 projects integrally upwardly. A semi-spherical recess 56 is defined in the bottom surface of the second end 26 of the clamp collar 22 to receive the sphere segment 54 therein and define a gap 58 therewith for allowing relative constricted angular movement between the pedicle screw 20 and the clamp collar 22. In one embodiment of the present invention, the angular movement of the pedicle screw 20 relative to the pin 30 is limited to approximately 28 degrees.

By directly articulating the pedicle screw 20 to the pin 30, the number of pieces to be assembled can be minimized in that the nut 40 cooperates with the pin 30 to retain the clamp collar 22 in secure engagement with one of the rods 12 and 14, while at the same time holding the pedicle screw 20 and the clamp collar 22 together.

As opposed to conventional orthopedic implantable systems wherein the anchors are locked in position relative to the associated fixation means after the rods have been fitted therethrough, the pedicle screw 20, illustrated in FIG. 2, is permanently articulated to the clamp collar 22. This greatly contributes to reduce the loads transmitted to the system 10 and, thus, eliminates the need of resorting to bone graft and spinal fusion to supplement the support offered by the system 10.

Figure 3:
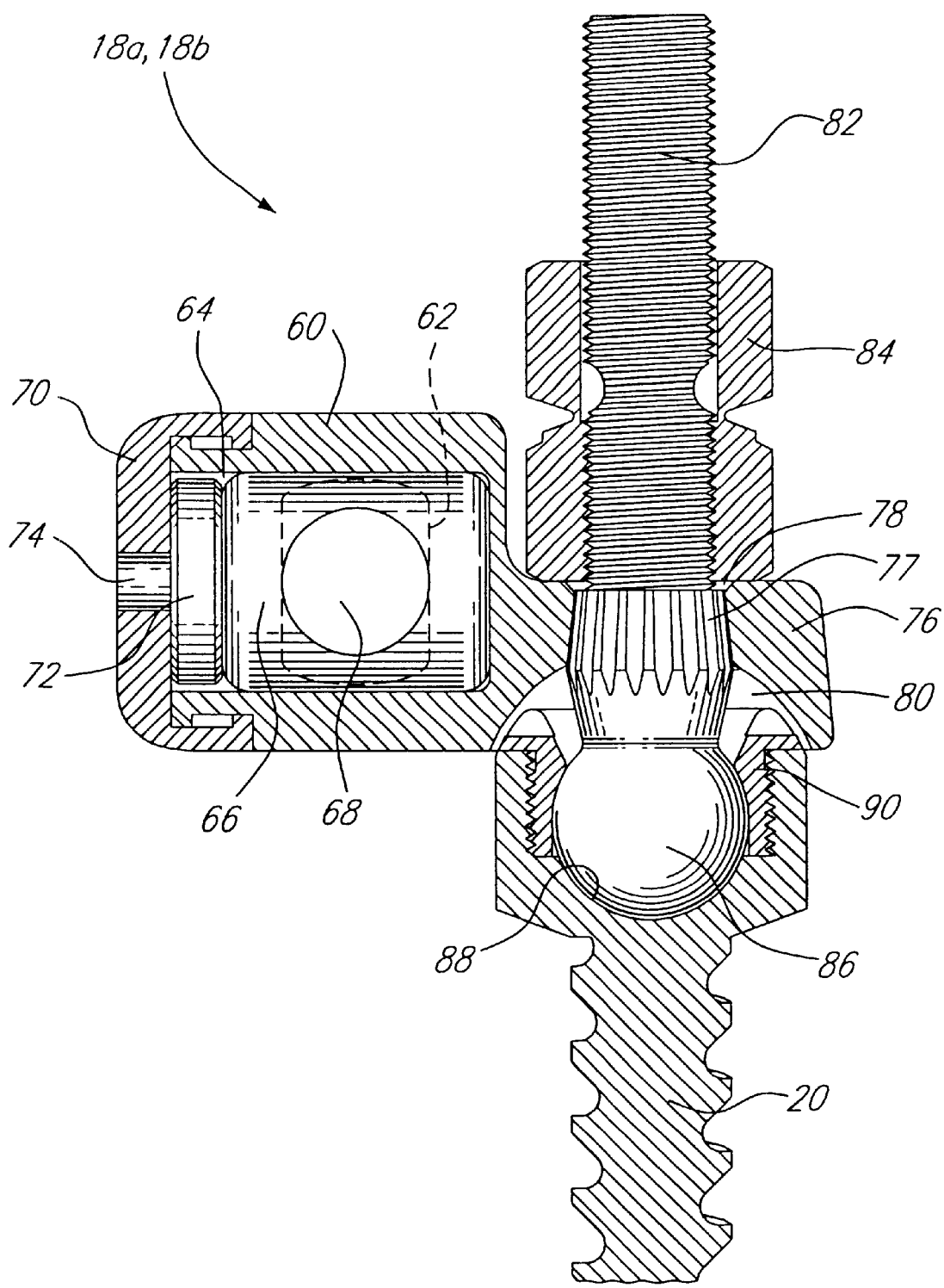
FIG. 3 is a cross-sectional view of a mobile pedicle screw carrier forming part of the mobile dynamic spinal instrumentation system of FIG. 1.

As seen in FIG. 3, each mobile carrier 18a, 18b includes a generally cylindrical body 60 defining a pair of opposed registered oblong holes or circumferentially extending slots 62 which communicate with a socket 64. A roller 66 having a transversal through bore 68 is received in the socket 64. The roller 66 is free to rotate about a longitudinal axis thereof within the socket 64. The roller 66 is retained captive within the socket 64 by means of a cap 70 securely engaged over an open end of the body 60. A polished bushing 72 is mounted to the inner side of the cap 70 to prevent axial movement of the roller 66 within the socket 64. The bushing 72 has an integral central pin projection 74 extending perpendicularly from one side thereof. The pin projection 74 is pressure fitted in a corresponding bore defined in the cap 70 for retaining the bushing 72 in position on the inner side of the cap 70.

A flat base projection 76 extends integrally axially from one end of the body 60 opposite the open end thereof. The base projection 76 has a bore 78 which communicates with a semi-spherical recess 80 defined in the underside surface of the base projection 76. A pin 82, similar to pin 30 illustrated in FIG. 2, extends through the bore 78 and the semi-spherical recess 80. A self-breaking and self-aligning nut 84 is threadably engaged on the pin 82 to couple the same to the base projection 76 of the body 60. A series of axially extending splines 77 are circumferentially distributed on an enlarged tapering portion of the pin 82 to mate with corresponding splines (not shown) formed on the side wall of the bore 78 in order to prevent the pin 82 from rotating about a longitudinal axis thereof relative to the base projection 76. The pin 82 is provided at one end thereof with a ball formation 86 adapted to be received in a socket 88 defined in the head of each pedicle screw 20, as explained hereinbefore with respect to the clamp collar 22. The ball formation 86 is retained captive in the socket 88 by means of a hollow retaining cap 90 similar to the retaining cap 50 illustrated in FIG. 2. The ball formation 86, the socket 88 and the retaining cap 90 form a ball and socket joint allowing the associated pedicle screw 20 to move in three degrees of freedom relative to the pin 82 and, thus, the body 60 of the mobile carrier 18a, 18b.

The body 60 is adapted to be mounted on rods 12 or 14 with the rod slidably received in the through bore 68 of the roller 66 and extending outwardly of the body 60 through the registered slots 62 thereof. Accordingly, the mobile carriers 18a and 18b can slide along the associated rods 12 and 14 and pivot relative thereto in a plane parallel to the sagittal plane of the spinal column S. The pivotal movement of the body 60 of each mobile carrier 18a, 18b relative to the rods 12 and 14 is limited by the spinal mobility.

The mobile carriers 18a have two degrees of freedom relative to the rod 12 and, likewise, the mobile carriers 18b have two degrees of freedom relative to the rod 14. The tilting capability of the mobile carriers 18a and 18b relative to the rods 12 and 14 along with the freedom of movements of the pedicle screws 20 relative to the body 60 of the mobile carriers 18a and 18b provide the required flexibility to ensure the translational mobility of the mobile carriers 18a and 18b along the rods 12 and 14. It is important that the mobile carriers 18a and 18b remain slidable on the rods 12 and 14 in order to permit spinal growth and some of the natural movement of the vertebrae and disc. The above described distribution of the degrees of freedom between the mobile carriers 18a and 18b and the rods 12 and 14, and the mobile carriers 18a and 18b and the pedicle screws 20 ensures that the mobile carriers 18a and 18b will not become locked against translational movement along the rods 12 and 14 once installed thereon.

As seen in FIG. 1, optional stoppers 92 can be fixedly secured to the ends of the rods 12 and 14 to prevent the mobile carriers 18a and 18b from sliding off the rods 12 and 14. An optional cross-link 94 can be installed between the rods 12 and 14 to prevent the same from pivoting apart, while allowing any other possible relative movements therebetween.

Figure 4:
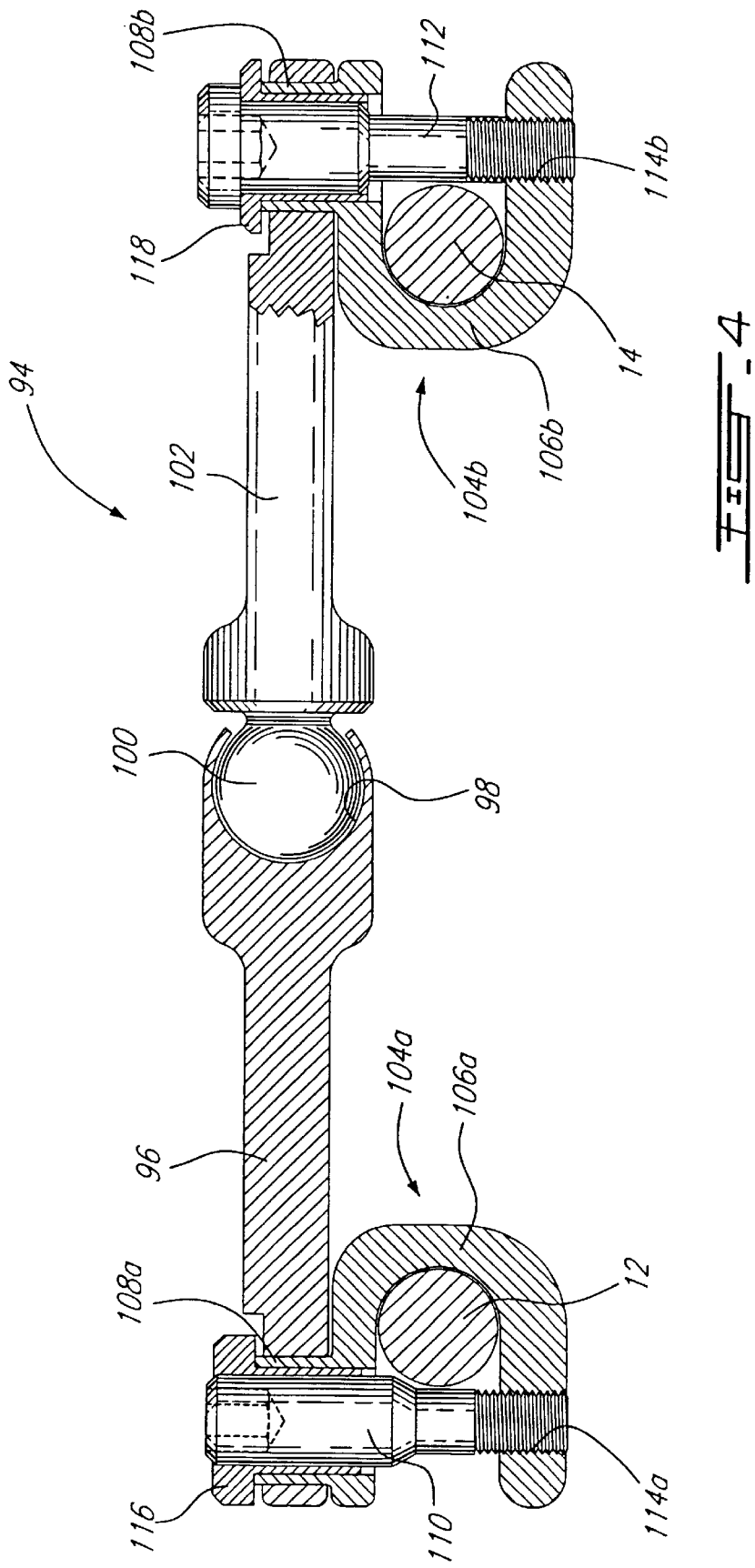
FIG. 4 is a cross-sectional view of an articulated cross-link forming part of the mobile dynamic spinal instrumentation system illustrated in FIG. 1.

As seen in FIG. 4, the cross-link 94 includes a first segment 96 having a proximal end defining a socket 98 for receiving a ball 100 integrally formed at a proximal end of a second segment 102. The ball 100 is freely rotatable in all directions within the socket 98, thereby providing an articulation between the first and second segments 96 and 102.

Rod engaging members 104a and 104b are provided at respective distal ends of the first and second segments 96 and 102. According to the illustrated embodiment, the rod engaging member 104a and 104b are provided in the form of hooks 106a and 106b having respective tubular projections 108a and 108b extending from one end thereof for selectively receiving a locking bolt 110 or a sliding bolt 112 depending whether it is desired to fixedly secure or slidably mount the cross-link 94 to the rods 12 and 14. For illustration purposes, the hook 106a is used in connection with a locking bolt 110, whereas the hook 106b is used in connection with a sliding bolt 112. In practice either a pair of sliding bolts 112 or a pair of locking bolts 110 could be simultaneously used or a combination of the two.

As seen in FIG. 4, the locking bolt 110 is threadably engaged within a threaded bore 114a defined in one end of the hook 106a opposite the tubular projection 108a thereof so as to wedge the rod 12 and lock the cross-link 94 in position thereon. Similarly, the sliding bolt 112 extends through the tubular projection 108b of the hook 106b to threadably engage a threaded bore 114b defined in the end of the hook 106b opposite the tubular projection 108b. However, the sliding bolt 112 only closes the mouth of the hook 106b without engaging the rod 14, thereby allowing the cross-link 94 to slide thereon.

A bushing 116 is fitted in the tubular projection 108a of the hook 106a about the locking bolt 110. Likewise, a bushing 118 is fitted in the tubular projection 108b of the hook 106b about the sliding bolt 112.

The mobile dynamic implantable instrumentation system 10 thus provides an implant which is adapted to be used without bone grafts and fusion, thereby preserving growth potential of the spinal column and bone as well as some of the natural mobility of the vertebrae and the disc thereof.

It is pointed out that according to a further embodiment of the present invention, the number of degrees of freedom between the pedicle screws 20 and the associated brackets 16a and 16b and the associated mobile carriers 18a and 18b could be limited to two.

Figure 5:
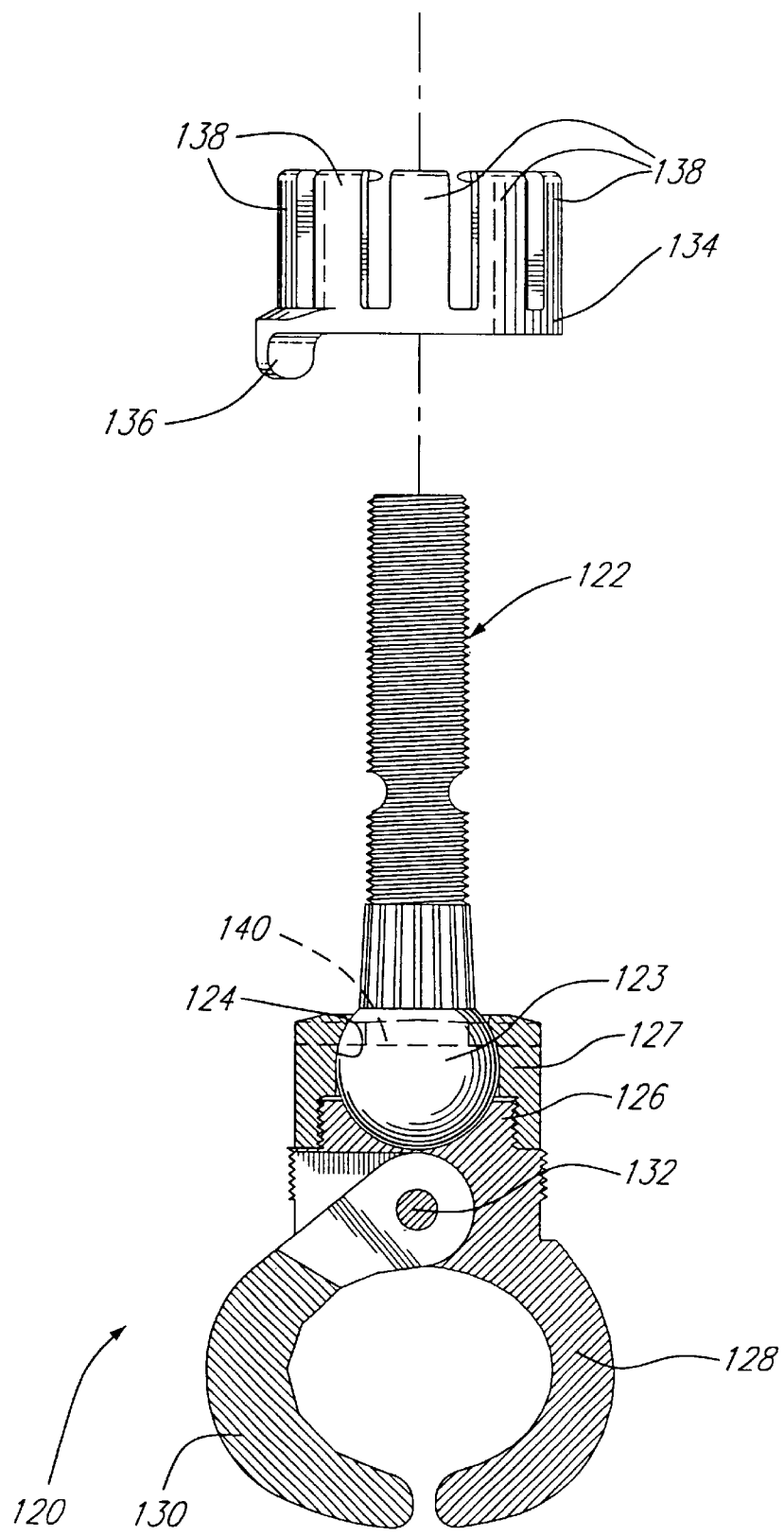
FIG. 5 is a cross-sectional view of a mobile transverse process hook sub-assembly adapted to be selectively articulately connected to a mobile carrier or a fixed bracket as an alternative to the pedicle screw sub-assembly shown in FIGS. 2 and 3.

As an alternative to the pedicle screws 20, a transverse process hook 120 (see FIG. 5) can be articulately mounted to each of the fixed brackets 16a, 16b and the mobile carriers 18a and 18b. The process hook 120 includes a pin 122 (similar to pin 30) having a ball formation 123 at one end thereof. The ball formation 123 is adapted to be trapped in a socket 124 defined in a cylindrical head portion 126 of a fixed arcuate gripping arm 128, thereby allowing limited relative movement between the pin 122 and the gripping arm 128. A cap 127 is threadably engaged on the head portion 126 to retain the ball formation 123 in the socket 124. A mobile gripping arm 130 is pivotally mounted to the fixed gripping arm 128 by means of a pivot pin 132 extending in a normal direction relative to the plane of the fixed gripping arm 128. A locking ring 134 is adapted to be threadably engaged on the cylindrical head portion 126 to push, via an integral depending tongue 136, on the mobile gripping arm 130 so as to cause the same to pivot towards the fixed gripping arm 128. In this way, the gripping arms 128 and 130 can be closed about a selected transverse process of a vertebrae in order to anchor an implantable spinal rod on one side of a spinal column. The opening of the gripping arms 128 and 130 is prevented from opening by the presence of the depending tongue 136 which acts as a stopper. A number of longitudinally extending bendable tabs 138 are distributed along an upper portion of the locking ring 134. Loosening of the locking ring 134 on the head portion 126 can be prevented by pressing a pair of diametrically opposed tabs 138 inwardly against corresponding diametrically opposed flattened portions 140 defined on the periphery of the cap 127. The threads of the cap 127 and the threads of the locking ring 134 are preferably opposite to prevent the latter from unlocking in the event that the cap 127 becomes loose on the head portion 126.

The process hook 120 can be readily installed on a fixed bracket 16a, 16b or a mobile carrier 18a, 18b by threadably engaging a nut, similar to nut 40, on the upper threaded portion of the pin 122, as described with respect to the pedicle screws 20 illustrated in FIGS. 2 and 3.

What is claimed is:

1. A mobile dynamic internal system for treating a disorder of a spinal column having a sagittal plane, comprising at least one implantable correcting rod for mounting on one side of a patient's spinal column, at least one fixed bracket rigidly mounted to said correcting rod, and at least one mobile carrier slidably mounted to said correcting rod on a selected side of said fixed bracket, and first and second anchors respectively mounted to said mobile carrier and said fixed bracket for anchoring said correcting rod to the spinal column, wherein, once said mobile dynamic internal system has been implanted, said first and second anchors still respectively have limited freedom of movement relative to said mobile carrier and said fixed bracket, thereby allowing said mobile carrier to slide along said correcting rod in response to movements of the spinal column.

2. A mobile dynamic internal system as defined in claim 1, wherein said mobile carrier is also mounted to said correcting rod for limited pivotal movement with respect thereto in a plane parallel to the sagittal plane of the spinal column.

3. A mobile dynamic internal system as defined in claim 2, wherein said mobile carrier includes a body defining a pair of opposed oblong holes disposed in registry and communicating with a socket formed within said body, a roller retained captive in said socket, said roller being free to rotate about a longitudinal axis thereof within said socket and defining a transversal through bore for slidably receiving said correcting rod therethrough, said transversal through bore being adapted to be placed in registry with said oblong holes for allowing said roller to be engaged on said correcting rod, and wherein pivotal movements of said body relative to said rod are limited by spinal mobility.

4. A mobile dynamic internal system as defined in claim 1, wherein said first anchor has three degrees of freedom relative to said mobile carrier.

5. A mobile dynamic internal system as defined in claim 4, wherein said first anchor is articulated to said mobile carrier by a ball and socket joint.

6. A mobile dynamic internal system as defined in claim 3, wherein said first anchor is articulated to said body of said mobile carrier at a location spaced-laterally from said oblong holes, said first anchor having a head defining a socket in which a ball secured to the body is retained captive.

7. A mobile dynamic internal system as defined in claim 6, wherein said head is at least partly received in a recess defined in a bottom surface of said body, said recess and said head defining a play for allowing limited relative movements between said first anchor and said body.

8. A mobile dynamic internal system as defined in claim 1, wherein said second anchor is articulated to said fixed bracket for limited angular relative movement with respect thereto.

9. A mobile dynamic internal system as defined in claim 1, wherein said mobile carrier has two degrees of freedom relative to said correcting rod, and wherein said first anchor has three degrees of freedom with respect to said mobile carrier.

10. A mobile dynamic internal system as defined in claim 9, wherein said mobile carrier is adapted to slide along said correcting rod and pivot with respect thereto in a plane parallel to the sagittal plane of the spinal column, and wherein said first anchor is articulated to said mobile carrier by a ball and socket joint.

11. A mobile dynamic internal system as defined in claim 1, wherein said fixed bracket includes a clamp collar adapted to be contracted in secure engagement with said correcting rod, and coupling means adapted to be engaged with said clamp collar to articulate said second anchor to said clamp collar, while at the same time securing said clamp collar to said correcting rod.

12. A mobile dynamic internal system as defined in claim 11, wherein said clamp collar extends between opposed first and second ends, and wherein said securing means include a pin extending through said first and second ends, and a nut adapted to be threadably engaged on said pin to draw said first and second ends towards each other, said pin being provided at one end thereof with a ball formation disposed on one external side of said first and second ends opposite said nut, said ball formation being received in a socket defined in said second anchor to form an articulated joint allowing for relative movements between said second anchor and said fixed bracket.

13. A mobile dynamic internal system as defined in claim 12, wherein said second anchor has a head, said socket being defined in said head.

14. A mobile dynamic internal system as defined in claim 1, further including an implantable stabilizing rod adapted to be mounted on one side of the spinal column opposite said correcting rod via a selected number of fixed brackets and mobile carriers, and a cross-link for articulately joining said correcting and stabilizing rods.

15. A mobile dynamic internal system as defined in claim 14, wherein said cross-link includes first and second links articulated to one another between said correcting and stabilizing rods.

16. A mobile dynamic internal system as defined in claim 15, wherein said first and second links are articulated to one another by a ball and a socket joint.

17. A mobile dynamic internal system as defined in claim 15, wherein said first and second links have respective rod coupling distal ends, each said rod coupling distal end being adapted to selectively cooperate with one of a locking member and a sliding member for respectively securing and slidably mounting said rod coupling distal end to a corresponding one of said correcting and stabilizing rods.

18. A mobile dynamic internal system as defined in claim 1, wherein stoppers are provided at opposed ends of said correcting rod to prevent said at least one mobile carrier from sliding off said correcting rod.

19. A mobile dynamic internal system as defined in claim 8, wherein said second anchor is articulated to said fixed bracket via a ball and socket joint.

20. A mobile dynamic internal system as defined in claim 1, wherein a selected number of mobile carriers are provided on opposed sides of a central fixed bracket.

21. A mobile dynamic anchoring assembly comprising an implantable rod, a carrier mounted to said implantable rod for sliding movement thereon and limited pivotal movement with respect thereto about an axis perpendicular to the rod, and a bone anchor articulately connected to said carrier for allowing the mobility of said carrier to be preserved once said anchor has been engaged with a bone.

22. A mobile dynamic anchoring assembly as defined in claim 21, wherein said carrier includes a body defining a pair of opposed oblong holes disposed in registry and communicating with a socket formed within said body, a roller mounted for free rotation in said socket, said roller defining a through bore for slidably receiving the rod therethrough, said through bore being adapted to be placed in registry with said oblong holes for allowing said roller to be engaged on the rod, and wherein said oblong holes are sized so that the pivotal movement of said body relative to the rod is limited by the mobility of the spine.

23. A mobile dynamic anchoring assembly as defined in claim 22, wherein said bone anchor is articulated to said body of said carrier at a location spaced-laterally from said oblong holes, said bone anchor having a head defining a socket in which a ball secured to the body is retained captive to form a ball and socket joint.

24. A mobile dynamic anchoring assembly as defined in claim 23, wherein said head is at least partly received in a semi-spherical recess defined in a bottom surface of said body, said semi-spherical recess and said head defining a play for allowing limited relative movements between said anchor and said body.

25. A mobile dynamic cross-link for structurally connecting a pair of implantable spinal rods together, comprising opposed first and second ends adapted to be connected to corresponding ones of a pair of implantable spinal rods, and a permanent point of articulation between said first and second ends to prevent the implantable spinal rods from pivoting apart while allowing any other limited relative movements therebetween in response to movements of a patient's spinal column.

26. A mobile dynamic cross-link as defined in claim 25, wherein said cross-link includes first and second links articulated to one another between the rods.

27. A mobile dynamic cross-link as defined in claim 26, wherein said first and second links are articulated to one another by a ball and a socket joint.

28. A mobile dynamic cross-link as defined in claim 25, wherein said first and second ends are adapted to selectively cooperate with one of a locking member and a sliding member for respectively securing and slidably mounting said cross-link to the implantable spinal rods.

* * * * *